United States Patent [19]
Carlier et al.

[11] Patent Number: 6,069,177
[45] Date of Patent: May 30, 2000

[54] 3-HYDROXY-PROPANAMINE DERIVED NEURONAL REUPTAKE INHIBITORS

[75] Inventors: Paul R. Carlier, Kowloon, The Hong Kong Special Administrative Region of the People's Republic of China; Elliott Richelson, Ponte Vedra Beach, Fla.; Ching Kam Lo, North Point, The Hong Kong Special Administrative Region of the People's Republic of China; Man Chu Lo, Cambride, Mass.

[73] Assignee: The Hong Kong University of Science and Technology, Kowloon, The Hong Kong Special Administrative Region of the People's Republic of China

[21] Appl. No.: 08/889,357

[22] Filed: Jul. 8, 1997

[51] Int. Cl.[7] .................................................. A01N 33/02
[52] U.S. Cl. ............................................. 514/652; 564/349
[58] Field of Search ............................... 514/652; 564/349

[56] References Cited

U.S. PATENT DOCUMENTS

| 4,018,895 | 4/1977 | Molloy et al. | 260/570.7 |
|---|---|---|---|
| 4,535,186 | 8/1985 | Husbands et al. | 564/336 |

OTHER PUBLICATIONS

Abstract to Carlier et al, "Anti–Selective Aldol Reaction of Benzylic Nitriles and Synthesis of gamma–Amino Alcohols", J. Org. Chem., 60(23), 7511–7517, 1995.

Carlier, P.R. et al, J. Org. Chem. 1995, 60, 7511.

*Primary Examiner*—Dwayne C. Jones
*Attorney, Agent, or Firm*—Jacobson, Price, Holman & Stern, PLLC

[57] ABSTRACT

3-Hydroxy-propanamine derivatives and acid salts thereof having chiral centers at the $C_1$ and $C_2$ positions exhibit synaptosomal reuptake inhibition of neurotransmitters, and as such represent a new class of psychotropic agents useful as antidepressants.

12 Claims, No Drawings

3-HYDROXY-PROPANAMINE DERIVED NEURONAL REUPTAKE INHIBITORS

The invention is a new class of antidepressant compounds which exhibit synaptosomal reuptake inhibition of neurotransmitters such as serotonin (5-HT), norepinephrine (NE), and dopamine (DA). The invention is a class of 3-hydroxy-propanamine compounds having chiral centers at the $C_1$ and $C_2$ positions.

BACKGROUND OF THE INVENTION

SSRI antidepressants such as Prozac® (Lilly), Paxil® (SKB) and Zoloft® (Pfizer), are characterized by an ability to selectively block reuptake of 5-HT. Selective NE-reuptake inhibitor antidepressants such as Tomoxetine (Lilly) and Vivalan® (Zeneca) have also been developed (Scheme 1).

Scheme 1

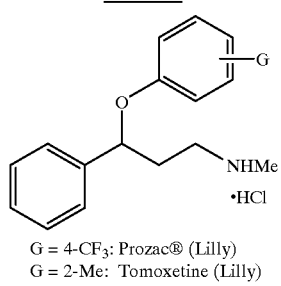

G = 4-CF₃: Prozac® (Lilly)
G = 2-Me: Tomoxetine (Lilly)

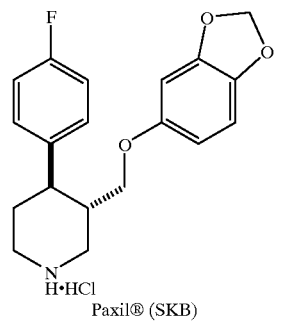

Paxil® (SKB)

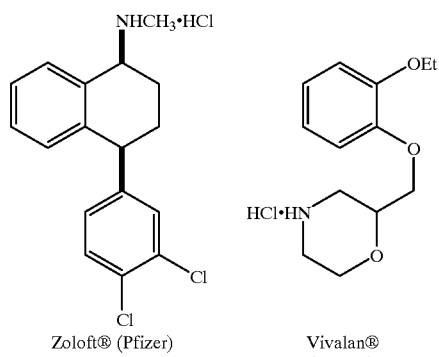

Zoloft® (Pfizer)          Vivalan® (Zeneca)

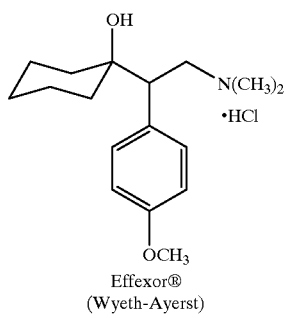

Effexor®
(Wyeth-Ayerst)

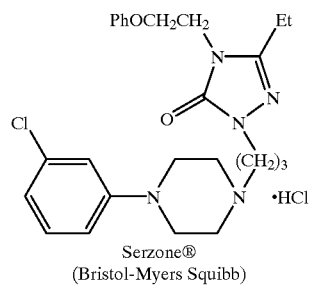

Serzone®
(Bristol-Myers Squibb)

Effexor® and Serzone® have been termed SNRI antidepressants because they inhibit 5-HT and NE reuptake with similar potency. To achieve an effective therapy for patients for whom present drugs are ineffective, it would be desirable to have drugs which possess reuptake inhibition profiles different from those currently known. Pinder and Wieringa have commented that an agent which simultaneously inhibits reuptake of 5-HT, NE, and DA could be the ultimate reuptake-inhibiting antidepressant drug (Med. Res. Rev., 13, 259–325 (1993)). The present invention provides the first examples of such drugs.

SUMMARY OF THE INVENTION

The compounds of the invention are 3-hydroxy-propanamine derivatives of the general structure I:

I

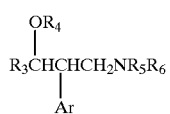

where Ar is any aromatic moiety of the structure:

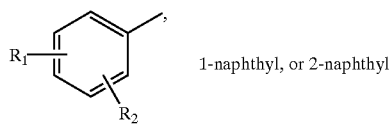

1-naphthyl, or 2-naphthyl $R_1$ and $R_2$ are independently hydrogen, $C_1$ to $C_6$ alkyl, $C_1$ to $C_6$ alkoxy, halo, dimethylamino, and trifluoro-methyl;

$R_3$ is $C_1$ to $C_{10}$ alkyl, or Ar according to the definition above;

$R_4$ is hydrogen, $C_1$ to $C_6$ alkyl, $C_1$–$C_6$ alkanoyl, or Ar according to the definition above; and $R_5$ and $R_6$ are independently hydrogen or $C_1$ to $C_6$ alkyl.

The preferred method of preparing compounds of the invention favours the formation of the anti-diastereomer. However, both syn- and , anti-diastereomers are included in the invention.

The pharmaceutically acceptable acid addition salts of the basic compounds of this invention are formed conventionally by reaction of the free base with an equivalent amount of any acid which forms a non-toxic salt. Illustrative acids are either inorganic or organic, including hydrochloric, hydrobromic, fumaric, maleic, succinic, sulfuric, phosphoric, tartaric, acetic, citric, oxalic, and similar acids. For parenteral administration, the use of water soluble salts is preferred. This invention covers the use of the racemic compounds, or use of either of the pure enantiomers.

The 3-hydroxy-propanamine substructure is found in a number of monoamine reuptake inhibiting antidepressants, as can be seen in Scheme 1. The compounds of the invention are structurally unique in that they feature an aryl group at C-2 and chiral centers at both C-2 and C-3.

DESCRIPTION OF THE INVENTION

The compounds of this invention are prepared by first reacting an aldehyde with the appropriate lithiated arylacetonitrile, according to the anti-selective aldol reaction of Carlier et al. (J. Org. Chem, 60, 7511 (1995)), followed by catalytic hydrogenation of the resulting racemic anti-2-hydroxynitrile, or treatment of the nitrile with aluminum chloride modified lithium aluminum hydride to give the corresponding racemic anti-3-hydroxy-propanamine (Carlier et al. J. Org. Chem, 60, 7511 (1995)). Pure enantiomers of these compounds may be prepared by classical resolution, using commercially available enantiomerically pure acids such as (+)- and (−)-tartaric acid, (+)- and (−)-ditoluyl-tartaric acid, and (+)- and (−)-camphorsulfonic acid. Synthesis of the N, N-dimethyl derivatives can be performed according to a modified Eschweiler-Clarke protocol (Kim et al. J. Org. Chem., 50, 1927 (1985)). N-methyl secondary amine derivatives can be prepared by reaction with ethyl chloroformate, and reduction of the carbamate intermediate with lithium aluminum hydride. Higher N-alkyl secondary amine derivatives can be prepared via the analogous amides, by substituting the appropriate alkanoyl chloride for ethyl chloroformate. Nonsymmetrical tertiary amine derivatives can be prepared by treatment of O-trimethylsilyl protected analogs of the previously mentioned carbamate or amide intermediates with sodium hydride in dimethylformamide, followed by the addition of an alkyl halide, prior to reduction. O-Alkyl amine derivatives can be prepared by treatment of the corresponding carbamate or amide derivatives with sodium hydride in dimethylformamide and addition of alkyl halide, prior to reduction. Synthesis of O-acyl derivatives can be effected via the Mitsunobu reaction, or in the case of tertiary aminoalcohols, by treatment of the free base with the appropriate alkanoyl chloride (or formic acetic anhydride in the case of formyl) in methylene chloride in the presence of catalytic 4-dimethylaminopyridine. Synthesis of O-aryl derivatives can be effected by the Mitsunobu reaction with the corresponding phenol (Gao et al. J. Org. Chem., 53, 4081 (1988)), or by nucleophilic aromatic substitution of the 3-hydroxy-propanamine alkoxide on the appropriate aryl fluoride or activated chloride (Koenig et al. Tetrahedron Lett., 35, 1339 (1994)).

Reuptake Inhibition in Rat Brain Synaptosomes

Inhibitor constants ($K_i$) for blockade of 5-HT, NE, and DA reuptake into rat brain synaptosomes were determined for a number of compounds of the invention as compared to various known compounds. Selected results are presented in Table 1, wherein compounds A-E are 3-hydroxy-propanamine derivatives of the general structure I according to the following Scheme 2:

Scheme 2

| | $R_3$ | Ar | $R_5,R_6$ | $R_4$ |
|---|---|---|---|---|
| A | t-Bu | 2-naphthyl | Me | H |
| B | Ph | 2-naphthyl | Me | H |
| C | t-Bu | 2-naphthyl | H | H |
| D | Ph | 2-naphthyl | H | H |
| E | c-$C_6H_{11}$ | 4-MeOPh | Me | H |

TABLE 1

$K_i$ Values from Rat Brain Synaptosomal Reuptake Experiments

| Compound[a] or Drug | 5-HT Reuptake $K_i$ (nM)[b] | NE Reuptake $K_i$ (nM)[c] | DA Reuptake $K_i$ (nM)[d] |
|---|---|---|---|
| A | 2.6 ± 0.3 | 10 ± 1 | 60 ± 10 |
| B | 4.1 ± 0.6 | 15 ± 2 | 12 ± 1 |
| C | 14 ± 2 | 44 ± 8 | 120 ± 10 |
| D | 27 ± 3 | 7.7 ± 0.2 | 6.2 ± 0.2 |
| E | 30 ± 5 | 220 ± 10 | 640 ± 60 |
| 5-HT | 18.5 ± 0.5 | — | — |
| NE | — | 119 ± 11.5 | — |
| DA | — | — | 65.1 ± 5.5 |
| Effexor ® | 37.2 ± 2.0 | 138 ± 7.5 | 360 ± 53.2 |
| Prozac ® | 14 ± 3 | 143 ± 6 | 3050 ± 70 |
| Paxil ® | 0.73 ± 0.04 | 33 ± 2 | 1700 ± 300 |
| Zoloft ® | 3.4 ± 0.4 | 220 ± 40 | 260 ± 4 |
| Tomoxetine | 43 ± 2 | 0.7 | 1400 ± 200 |
| Serzone ® | 137 ± 4 | 570 ± 50 | 2380 ± 80 |

Effexor® was chosen as a control because it bears the closest structural resemblance to the compounds described in this invention. Rat brain synaptosomal uptake data for the other known antidepressants listed in Table 1 were taken from C. Bolden-Watson and E. Richelson (Life Science, 53, p. 1023–1029 (1993)). As can be seen in Table 1, compounds A, B, and D are remarkable in that they block uptake of all three neurotransmitters (5-HT, NE, and DA) with $K_i$ values in the nanomolar to 10 nanomolar range. The highest $K_i$ value exhibited by compounds A, B, and D is 60 nM, for dopamine reuptake inhibition by compound A. It can be seen that none of the known antidepressants listed in Table 1 exhibit such low $K_i$ values in all three assays.

To define a quantitative basis for determining whether a compound offers simultaneous potent inhibition of reuptake of all three neurotransmitters, reuptake inhibition potency values were calculated by dividing the reuptake $K_i$ value for the natural substrate (5-HT, NE or DA) by the reuptake $K_i$ of the drug or compound being assayed (Table 2):

TABLE 2

Reuptake Inhibition Potency Values from Rat Brain Synaptosomal Reuptake Experiments

| Compound[a] or Drug | 5-HT (Rat) Reuptake Inhibition Potency[b] | NE (Rat) Reuptake Inhibition Potency[c] | DA (Rat) Reuptake Inhibition Potency[d] | Simultaneous Reuptake Inhibition Potency[e] |
|---|---|---|---|---|
| A | 7.23 | 12.0 | 1.11 | yes |
| B | 4.48 | 7.88 | 5.38 | yes |
| C | 1.37 | 2.74 | 0.57 | no |
| D | 0.68 | 15.5 | 10.5 | no |

TABLE 2-continued

Reuptake Inhibition Potency Values from Rat
Brain Synaptosomal Reuptake Experiments

| Compound[a] or Drug | 5-HT (Rat) Reuptake Inhibition Potency[b] | NE (Rat) Reuptake Inhibition Potency[c] | DA (Rat) Reuptake Inhibition Potency[d] | Simultaneous Reuptake Inhibition Potency[e] |
|---|---|---|---|---|
| E | 0.62 | 0.54 | 0.10 | no |
| 5-HT | 1.0 | — | — | |
| NE | — | 1.0 | — | |
| DA | — | — | 1.0 | |
| Effexor ® | 0.50 | 0.86 | 0.18 | no |
| Prozac ® | 1.32 | 0.83 | 0.02 | no |
| Paxil ® | 25.3 | 3.61 | 0.04 | no |
| Zoloft ® | 5.44 | 0.54 | 0.25 | no |
| Tomoxetine | 0.43 | 170 | 0.05 | no |
| Serzone ® | 0.14 | 0.21 | 0.03 | no |

[a]Compounds A–E are racemic. Reuptake inhibition potency values for Prozac® to Serzone® are derived from $K_i$ values in C. Bolden-Watson and E. Richelson, Life Sciences, 52, 1023–1029 (1993).

[b]Defined as $K_i$(5-HT)/$K_i$(compound or drug) in the 5-HT reuptake inhibition assay.

[c]defined as $K_i$(NE)/$K_i$(compound or drug) in the NE reuptake inhibition assay.

[d]Defined as $K_i$(DA)/$K_i$(compound or drug) in the DA reuptake inhibition assay.

[e]A compound or drug is considered to possess simultaneous reuptake inhibition potency if each of the potency values is greater than 1.0.

A compound or drug is considered to possess "simultaneous reuptake inhibition potency" if each of the reuptake inhibition values is greater than 1.0. According to this criterion, compounds A and B possess the quality of "simultaneous reuptake inhibition potency". In contrast, none of the known antidepressant drugs listed in Table 2 possesses this quality. These data, therefore, support the view that the invention provides an entirely new class of antidepressants.

Binding to Molecularly Cloned Human Transporter Proteins

To further substantiate the unique nature of the antidepressants of the invention, it is useful to produce evidence of simultaneous reuptake inhibition potency in human brain. To this end the binding of compounds of the invention to the molecularly cloned human transporters for 5-HT, NE, and DA (hSERT, hNET, and hDAT respectively) have been studied. These transporters are responsible for neuronal reuptake of the neurotransmitters. A low equilibrium dissociation constant $K_d$ for a compound indicates strong binding to the transporter and consequent excellent reuptake inhibition by the compound (Table 3):

TABLE 3

Equilibrium Dissociation Constants $K_d$ with the
Molecularly Cloned Human Transporter Proteins
for 5-HT, NE, and DA

| Compound[a] or Drug | hSERT $K_d$(nM)[b] | hNET $K_d$(nM)[c] | hDAT $K_d$(nM)[d] |
|---|---|---|---|
| A | 1.2 ± 0.9 | 29.9 ± 0.4 | 340 ± 10 |
| B | 5.59 ± 0.02 | 44 ± 2 | 70 ± 8 |
| C | 6.1 ± 0.3 | 55 ± 1 | 27,000 ± 2,000 |
| D | 6.2 ± 0.3 | 21 ± 2 | 140 ± 20 |
| E | 30.0 ± 0.9 | 1800 ± 10 | 3,500 ± 200 |

TABLE 3-continued

Equilibrium Dissociation Constants $K_d$ with the
Molecularly Cloned Human Transporter Proteins
for 5-HT, NE, and DA

| Compound[a] or Drug | hSERT $K_d$(nM)[b] | hNET $K_d$(nM)[c] | hDAT $K_d$(nM)[d] |
|---|---|---|---|
| 5-HT | 2,100 ± 100 | — | — |
| NE | — | 2200 ± 30 | — |
| DA | — | — | 2,400 ± 100 |
| Effexor ® | 8.9 ± 0.3 | 1,060 ± 40 | 9,300 ± 60 |
| Prozac ® | 0.81 ± 0.015 | 240 ± 10 | 3,600 ± 100 |
| Paxil ® | 0.125 ± 0.009 | 40 ± 2 | 500 ± 20 |
| Zoloft ® | 0.293 ± 0.008 | 420 ± 20 | 25 ± 2 |
| Imipramine | 0.90 ± 0.08 | — | — |
| Nisoxetine | — | 1.8 ± 0.1 | — |
| WIN35428 | — | — | 21.6 ± 0.8 |

[a]Compounds A–E are racemic.

[b]by displacement of [$^3$H]imipramine from molecularly cloned hSERT.

[c]by displacement of [$^3$H]nisoxetine from molecularly cloned hNET.

[d]by displacement of [$^3$H]WIN35428 from molecularly cloned hDAT.

It can be seen that compounds A–D bind very tightly to hSERT and hNET, with $K_d$ values in the nanomolar to ten nanomolar range. Compound B is again seen to be remarkable, having affinities for all three transporters in the nanomolar or ten nanomolar range. To assess the overall performance of compounds A–E, these data can be expressed in the form of potency values, relative to the natural substrates (Table 4):

TABLE 4

Transporter Binding Potency Values

| Compound[a] or Drug | hSert Binding Potency[b] | hNet Binding Potency[c] | hDAT Binding Potency[d] | Simultaneous Transporter Binding Potency[e] |
|---|---|---|---|---|
| A | 1,750 | 73.6 | 7.16 | yes |
| B | 376 | 50.6 | 34.3 | yes[f] |
| C | 347 | 39.9 | 0.09 | no |
| D | 340 | 103 | 16.8 | yes |
| E | 70 | 1.24 | 0.69 | no |
| 5-HT | 1.0 | — | — | |
| NE | — | 1.0 | — | |
| DA | — | — | 1.0 | |
| Effexor ® | 235 | 2.08 | 0.26 | no |
| Prozac ® | 2,590 | 9.17 | 0.67 | no |
| Paxil ® | 16,800 | 55 | 4.80 | no |
| Zoloft ® | 7,170 | 5.24 | 96.0 | no |

[a]Compounds A–E are racemic.

[b]Defined as $K_d$(5-HT)/$K_d$(compound or drug) in the hSERT binding assay.

[c]Defined as $K_d$(NE)/$K_d$(compound or drug) in the hNET binding assay.

[d]defined as $K_d$(DA)/$K_d$(compound or drug) in the hDAT binding assay.

[e]A compound or drug is considered to possess "simultaneous transporter binding potency" if each of the potency values is greater than 7.0.

[f]Still retains "simultaneous transporter binding potency" if the criterion is tightened to mean all potency values must be greater than 30.

As Table 4 illustrates, the natural substrates exhibit rather low affinity for their respective transporters, resulting in significantly larger potency values in the human model (Table 4) than in rat (Table 2). One may therefore define "simultaneous transporter binding potency" to mean that each of the transporter binding potency values for 5-HT, NE, and DA must be ≧7.0. Using this criterion compounds A, B, and D qualify for simultaneous transporter binding potency, and none of the known antidepressant drugs tested qualify. Note that if the criterion for "simultaneous transporter binding potency" is tightened to mean all potencies must be greater than 30, then compound B still qualifies, and the contrast between it and known antidepressants is further enhanced.

SUMMARY

Compounds A and B potently inhibit reuptake of all three neurotransmitters in both the rat and human models. Compound D meets the criterion for simultaneous transporter binding potency in the human model, but narrowly misses the criterion for simultaneous reuptake inhibition potency in the rat model. (Table 5):

TABLE 5

Comparison of Rat and Human Data

| Compound or Drug | Simultaneous Reuptake Inhibition Potency (Rat) | Simultaneous Transporter Binding Potency (Human) |
| --- | --- | --- |
| A | yes | yes |
| B | yes | yes |
| C | no | no |
| D | no[a] | yes |
| E | no | no |
| Effexor ® | no | no |
| Prozac ® | no | no |
| Paxil ® | no | no |
| Zoloft ® | no | no |

[a]Meets reuptake inhibition potency criterion for NE and DA; reuptake inhibition potency for 5-HT is 0.68.

None of the currently available antidepressant drugs possess either simultaneous reuptake inhibition potency in rat, or simultaneous transporter binding potency in human. Thus, it has been demonstrated that compounds described in this invention represent the first members of a new class of "super-antidepressants", which may have a faster onset of activity and be useful in the treatment of refractory patients.

The data presented indicate that the compounds of the invention possess a pharmacologic activity comparable to or surpassing that of known antidepressant drugs. Accordingly the invention also includes the use of compounds of formula I for the treatment of depression, anxiety disorders (including panic disorder, obsessive compulsive disorder, generalized anxiety disorder), and related disorders which are influenced by brain serotoninergic neural systems. Thus, compounds of formula I may be useful for the treatment of sleep disorders, sexual dysfunction, and appetite disorders as part of the more general mental malaise known as depression.

Treatment of depression using compounds of the invention having the general formula I may be effected through pharmaceutical compositions formulated for administration orally or parenterally in a dosage sufficient to alleviate the depression symptoms. In this regard compounds of formula I including pharmaceutically acceptable salts thereof, may be combined with acceptable fillers, tabletting agents, solvents, emulsifiers, carriers, flavour enhancers and the like, all of which will be apparent to the skilled person. Pharmaceutical compositions of the invention will preferably be provided in unit dosage form.

Rat Brain Assay Methods

Inhibition of reuptake of the neurotransmitters in rat brain synaptosomes was performed according to the literature procedure (C. Bolden-Watson and E. Richelson, Life Sciences, 52, 1023–1029 (1993)):

Synaptosomal Preparation

Male Sprague-Dawley rats (125–250 g) from Harlan Sprague-Dawley (Indianapolis, Ind., USA) were decapitated and either the cortical ([$^3$H]5-HT), striatal ([$^3$H]DA), or hippocampal ([$^3$H]NE) tissues were rapidly dissected. A crude synaptosomal ($P_2$) fraction was prepared as described by others (Gray et al. J. Anat., 96, 79–88 (1962)). Briefly, the tissue was homogenized in 20 volumes of ice-cold 0.32 M sucrose containing 11 mM glucose, pH 7.4 in a glass Potter-Elvehjem homogenizer with teflon pestle (8 strokes, 900 rpm). The homogenate was centrifuged at 1,000 g for 10 minutes. The resulting supernatant was then centrifuged at 20,000 g for 20 minutes and the supernatant was discarded. The pellet ($P_2$) was gently resuspended in oxygenated incubation buffer at pH 7.4 containing 10 mM glucose, 20 mM HEPES, 145 mM NaCl, 4.5 mM KCl, 1.2 mM $MgCl_2$, and 1.5 mM $CaCl_2$ for assays.

Uptake Assays

Uptake assays were performed as a modification of the methods of Richelson et al. (Eur. J. Pharmacol., 104, 277–286 (1984)) and Baker et al. (J. Neurochem., 50, 1044–1052 (1988)). Levo-[ring-2,5,6-$^3$H]NE (43.7 Ci/mmol) and 5-[1,2-$^3$H (N)]hydroxytryptamine binoxalate (23.4 Ci/mmol) were obtained from New England Nuclear (Boston, Mass., USA), and [7,8-$^3$H]DA (47 Ci/mmol) was obtained from Amersham (Arlington Heights, Ill.). Briefly, synaptosomal protein (1.0–2.5 mg) was suspended in a total volume of 1 mL containing oxygenated incubation buffer, 10 $\mu$M pargyline to inhibit monoamine oxidase activity, 0.2 mg/mL sodium ascorbate and varying concentrations of other compounds or drugs as indicated in the text. The assay tubes contained 8 nM [$^3$H]NE plus 50 nM of NE, 4 nM [$^3$H]5-HT, or 2 nM [$^3$H]DA. After a 5 minute preincubation at 37° C. in a shaking water bath (80 oscillations/minute), the uptake was initiated by the addition of the synaptosomal protein. The reaction was stopped after 5 minute by adding 4 mL ice-cold 0.9% (w/v) sodium chloride and rapidly filtered through a Whatman GF/B glass fiber filter in a 48-place Brandel cell harvester. The filter was then washed with an additional 8 mL of wash buffer, placed in a scintillation vial containing 5 mL of Redi-Safe (Beckman Instruments, Fullerton, Calif.) and counted. Specific uptake was calculated as the difference between the total uptake (zero unlabelled ligand) and nonspecific uptake (excess unlabelled ligand).

Cell Culture for Expression of Human Neurotransmitter Proteins

Cells expressing the human norepinephrine transporter (hNET) (Pacholczyk et al. Nature, 350, 350–354, (1991)), the human dopamine transporter (hDAT) (Pristupa et al. Mol. Pharmacol., 45, 125–135, (1994)), and the human serotonin transporter (hSERT) (Ramamoorthy et al. Proc. Natl. Acad. Sci. U. S. A. 90, 2542–2546, (1993)) were grown and passaged in 150-mm petri dishes in 17.5 ml of Dulbecco's modified Eagle's medium (Mediatech Inc.) containing 0.1 mM Non-Essential Amino Acid Solution for MEM (Mediatech Inc.), 5% (v/v) Fetal Clone Bovine serum product (Hyclone Laboratories, Logan, Utah), and 1 U/$\mu$L Penicillin and Streptomycin Solution (Mediatech Inc.). Cells were incubated in 10% $CO_2$, 90% air at 37° C. and 100% humidity. The selecting antibiotic geneticin sulfate (250 µg/ml) was used during the cell culture for the hNET only.

Preparation of Membranes from Cells for Human Transporter Binding Studies

For the preparation of homogenates, medium was removed by aspiration. Cells were washed with 4 mL modified Puck's D1 solution (solution 1) (Richelson et al. in "Methods in Neurotransmitter Receptor Analysis" Yamamura, H. I.; Enna, S. J.; Kuhar, M. J. Eds.; New York, Raven Press, 1990, pp 147–175) and then incubated for 5 min at 37° C. in 10 mL solution 1 containing 100 mM ethylene glycol-bis N,N,N',N'-tetraacetic acid (EGTA). Cells were then scraped from the surface with a rubber spatula into a centrifuge tube and collected by centrifugation at 1000×g for 5 min at 4° C. Supernatants were decanted and the pellet was resuspended in the appropriate binding buffer and homogenized with the use of a Polytron for 10 sec at setting 6. This solution was centrifuged at about 36,000×g for 10 minutes (4° C.). The pellet was suspended in the same volume of buffer and the centrifugation was repeated. The supernatants were decanted and the final pellet was suspended in the appropriate buffer and stored at −80° C. until use. The final protein concentration was determined by the Lowry assay (Lowry et al. J. Biol. Chem. 193, 265–275 (1951)), using bovine serum albumin as a standard.

Radioligand Binding Assay for Human Transporter Proteins

[$^3$H]imipramine binding to cloned human SERT.

This binding assay was performed by a modification of the method of O'Riordan et al. (J. Neurochem., 54, 1275–80, (1990)). For the membranal preparation, cells were homogenized in 50 mM Tris-HCl with 120 mM NaCl and 5 mM KCl (pH 7.4). For the assay about 15 µg protein of the membranal preparation was used with about 1.0 nM [$^3$H] imipramine (imipramine hydrochloride, benzene ring-$^3$H, specific activity 46.5 Ci/mmol, Dupont New England Nuclear, Boston, Mass.) and varying concentrations of unlabeled imipramine or other drugs being tested. Nonspecific binding was determined with 1 µM final concentration of unlabeled imipramine in the assay tubes. The reaction mixture was incubated at 22° C. for 30 min. The assay was terminated by rapid filtration of the contents of each tube through a GF/B filter strip, which had been pretreated with 0.2% polyethylenimine, with the use of a 48-well Brandel cell harvester. The filter strips were then rinsed five times with ice-cold 0.9% NaCl. Next, individual filters were cut from the strip and placed in a scintillation vial containing 6.5 mL of Redi-Safe (Beckman Instruments, Fullerton, Calif.). Radioactivity was measured with a Beckman liquid scintillation counter (LS 5000TD).

[$^3$H]nisoxetine binding to cloned human NET.

This binding assay was performed by a modification of the method of Jayanthi et al. (Biochemistry, 32, 12178–85, (1993)). For the membranal preparation, cells were homogenized in 50 mM Tris-HCl with 300 mM NaCl and 5 mM KCl (pH 7.4). For the assay about 25 µg protein of membranal preparation was used, with about 0.5 nM [$^3$H] nisoxetine (nisoxetine HCl, [N-methyl-$^3$H], specific activity 85.0 Ci/mmol, Amersham, Arlington Hts., Ill.), and varying concentrations of the unlabeled nisoxetine or other drugs being tested. Nonspecific binding was determined with 1 µM final concentration of unlabeled nisoxetine. The reaction mixture was incubated at 22° C. for 60 min. The remaining methods were exactly as described for hSERT above.

[$^3$H]WIN35428 binding to cloned human DAT.

This binding assay was performed by a modification of the methods of Pristupa et al. (Mol Pharmacol., 45, 125–135, (1994)). For the membranal preparation, cells were homogenized in the 50 mM Tris-HCl with 120 mM NaCl (pH 7.4). For the assay about 30 µg protein of the membranal preparation was used, with about 1 nM [$^3$H]WIN35428 (WIN35428, [N-methyl-$^3$H], specific activity 83.5 Ci/mmol, Dupont New England Nuclear, Boston, Mass.), and varying concentrations of the unlabeled WIN35428 or other drugs being tested. Nonspecific binding was determined with 10 µM final concentration of unlabeled WIN35428. The reaction mixture was incubated at 4° C. for 2 hr. The remaining methods were exactly as described for hSERT above.

Data Analysis

Data analysis was performed using the LIGAND program (P. Munson and D. Rodbard, Analyt. Biochem., 107, 220–239, (1980)) to provide values for the equilibrium dissociation constants (KD'S). The program was modified by the inventors to calculate the Hill Coefficient (nH). Data are presented as geometric mean ±S.E.M. (De Lean et al. Mol. Pharmacol., 21, 5–16, 1982, and Fleming et al. J. Pharmacol. Exp. Ther., 181, 339–345, 1972)) of at least 3 independent experiments. One-component models and two-component models were compared using the root mean square error of each fit and the F test.

Synthetic Procedures

EXAMPLE 1

(2RS,3RS)-3-hydroxy-4,4-dimethyl-2-(2'-naphthyl) pentane-nitrile

A 250 mL round bottom flask equipped with magnetic stirring bar and septum was charged with tetrahydrofuran (80 mL), 2-naphthylacetonitrile (5.095 g, 30.5 mmol), purged with nitrogen, and cooled to −78° C. A solution of lithium diisopropylamide (2.0 M, 16.5 mL, 33.0 mmol) was added and stirred for 30 minutes. Pivalaldehyde (3.4 mL, 31.4 mmol) was added, and after an additional 30 minutes the reaction was quenched by addition of saturated aqueous ammonium chloride (25 mL). After warming to room temperature, the reaction was diluted with 50 mL 1 N hydrochloric acid, and then extracted with diethyl ether (4×25 mL). The combined organic extracts washed with saturated brine (20 mL) and dried (magnesium sulfate). Finally, concentration in vacuo afforded the crude aldol. Recrystallization from toluene/hexane gave 5.41 g (70%) of the desired anti-aldol product, mp: 90.4–91.7° C. NMR ($^1$H, $^{13}$C), IR, and Mass spectra were consistent with the assigned structure. Analysis: Calcd for $C_{17}H_{19}NO$: C, 80.60; H, 7.56; N, 5.53. Found: C, 80.63; H, 7.56; N, 5.48.

EXAMPLE 2

(2RS,3RS)-3-hydroxy-4,4-dimethyl-2-(2'-naphthyl)pentyl-ammonium chloride (Compound C)

A solution of aluminum chloride (1.437 g, 10.7 mmol) in diethyl ether (20 mL) was transferred via cannula into a suspension of lithium aluminum hydride (390.7 mg, 10.3 mmol) in diethyl ether (20 mL) in a 250 mL round bottomed flask under nitrogen at room temperature. A solution of (2RS,3RS)-3-hydroxy-4,4-dimethyl-2-(2'-naphthyl) pentane-nitrile (1.03 g, 4.08 mmol) in diethyl ether (20 mL) was then added by cannula to this mixture over 5 minutes. After stirring for 21 hours at room temperature the reaction was quenched by sequential addition of ethyl acetate (5 mL) and 10% sulfuric acid (80 mL). The mixture was stirred vigorously to ensure complete dissolution of the aluminate precipitate. The aqueous phase was separated, washed with diethyl ether (40 mL), and then basified with excess sodium hydroxide pellets at 0° C. The aqueous layer was extracted with diethyl ether (4×100 mL) and the diethyl ether extract was washed with saturated brine and dried (potassium carbonate), and concentrated in vacuo to afford 0.919 g (88%) of the desired primary amine free base (oil). Dissolution in diethyl ether, treatment with dry hydrogen chloride gas and concentration in vacuo afforded the corresponding hydrochloride salt, mp 247° C. (decomp.). NMR ($^1$H, $^{13}$C), IR, and Mass spectra were consistent with the assigned structure. Analysis (as mono-3,5-dinitrobenzoate): Calcd for $C_{24}H_{25}N_3O_6$: C, 63.85; H, 5.58; N, 9.31. Found: C, 63.71; H, 5.67; N, 9.19.

EXAMPLE 3

(2RS,3RS)-3-Hydroxy-4,4-dimethyl-2-(2'-naphthyl)pentyl-N, N-dimethyl-ammonium chloride (Compound A)

To a solution of (2RS,3RS)-3-hydroxy-4,4-dimethyl-2-(2'-naphthyl)pentylammonium chloride (1.11 mmol) in methanol was added formaldehyde solution (0.28 mL, 3.4 mmol), and a solution of sodium cyanoborohydride (189.7 mg, 3.02 mmol) and zinc chloride (161.7 mg, 1.19 mmol) in methanol. The reaction mixture was stirred for 6 hours, and then basified with 50 mL 2 M sodium hydroxide. It was extracted with 3×50 mL diethyl ether, and the diethyl ether extract was washed with saturated brine and dried (potassium carbonate). Treatment with dry hydrogen chloride gas and concentration in vacuo afforded 0.351 g (98%) of the pure N,N-dimethyl-3-hydroxy-propanamine hydrochloride salt, mp 185.3–189.0° C. NMR ($^1$H, $^{13}$C), IR, and Mass spectra were consistent with the assigned structure. Analysis: Calcd for $C_{19}H_{28}ClNO$: C, 70.90; H, 8.77; N, 4.35. Found: C, 70.85; H, 8.68; N, 4.63.

EXAMPLE 4

(2RS,3RS)-3-Hydroxy-2-(2'-naphthyl)-3-phenyl-propionitrile

Reaction of 2-naphthylacetonitrile and benzaldehyde on a 15 mmol scale according to the procedure in Example 1, and two successive recrystallizations from methylene chloride/hexane gave 2.57 g (63%) of the desired anti-aldol product, mp 151.8–153.1° C. NMR ($^1$H, $^{13}$C), IR, and Mass spectra were consistent with the assigned structure. Analysis: Calcd for $C_{19}H_{15}NO$: C, 83.49; H, 5.53; N, 5.12. Found: C, 83.47; H, 5.44; N, 4.94.

EXAMPLE 5

(2RS,3RS)-3-Hydroxy-2-(2'-naphthyl)-3-phenyl-propylammonium chloride (Compound D)

Following the procedure described in Example 2, reduction of 4.4 mmol of (2RS,3RS)-3-Hydroxy-2-(2'-naphthyl)-3-phenyl-propionitrile gave 0.902 g (65%) of the desired primary amine hydrochloride, mp 215° C. (decomp.). NMR ($^1$H, $^{13}$C), IR, and Mass spectra were consistent with the assigned structure. Analysis: Calcd for $C_{19}H_{20}ClNO$: C, 72.72; H, 6.42; N, 4.46. Found: C, 72.62; H, 6.44; N, 4.50.

EXAMPLE 6

(2RS,3RS)-3-Hydroxy-2-(2'-naphthyl)-3-phenylpropyl-N, N-dimethylammonium chloride (Compound B)

Following the procedure described in Example 3, reductive methylation of 0.99 mmol of (2RS,3RS)-3-Hydroxy-2-(2'-naphthyl)-3-phenyl-propylammonium chloride gave 0.333 g (98%) of the desired tertiary amine hydrochloride, mp 212.8–215.3° C. NMR ($^1$H, $^{13}$C), IR, and Mass spectra were consistent with the assigned structure. HRMS (CI+): Calcd for $C_{21}H_{24}NO$ (M-Cl): 306.18579. Found: 306.18508.

EXAMPLE 7

(2RS,3SR)-3-cyclohexyl-3-hydroxy-2-(4'-methoxyphenyl)-propionitrile

Reaction of p-methoxyphenylacetonitrile and cyclohexane-carboxaldehyde on a 20 mmol scale according to the procedure in Example 1, and two successive recrystallizations from chloroform/hexane gave 3.51 g of the desired anti-aldol product (68%), mp: 112.0–113.2° C. NMR ($^1$H, $^{13}$C), IR, and Mass spectra were consistent with the assigned structure. Analysis: Calcd for $C_{16}H_{21}NO_2$: C, 74.10; H, 8.16; N, 5.40. Found: C, 74.25; H, 8.15; N, 5.39.

EXAMPLE 8

(2RS,3SR)-3-cyclohexyl-3-hydroxy-2-(4'-methoxyphenyl)-propylammonium chloride

Following the procedure in Example 2, 2.06 mmol of (2RS, 3SR)-3-cyclohexyl-3-hydroxy-2-(4'-methoxyphenyl)-propionitrile were reduced, affording 0.574 g (93%) of the desired primary amine hydrochloride, mp 207.2–208.5° C. NMR ($^1$H, $^{13}$C), IR, and Mass spectra were consistent with the assigned structure. Analysis: Calcd for $C_{16}H_{26}ClNO_2$: C, 64.09; H, 8.74; N, 4.67. Found: C, 63.88; H, 8.72; N, 4.63.

EXAMPLE 9

(2RS,3SR)-3-Cyclohexyl-3-hydroxy-2-(4'-methoxyphenyl)-propyl-N,N-dimethylammonium chloride (Compound E)

Following the procedure described in Example 3, reductive methylation of 0.6 mmol of (2RS,3SR)-3-cyclohexyl-3-hydroxy-2-(4'-methoxyphenyl)propylammonium chloride afforded 0.188 g (96%) of the desired tertiary amine hydrochloride (oil). NMR ($^1$H, $^{13}$C), IR, and Mass spectra were consistent with the assigned structure. Analysis: Calcd for $C_{18}H_{30}ClNO_2$: C, 65.94; H. 9.22; N, 4.27. Found: C, 65.67; H, 9.45; N, 5.14. HRMS (CI+): Calcd for $C_{18}H_{30}NO_2$ (M-Cl) : 292.22765. Found: 292.22793.

EXAMPLE 10

(2RS,3RS)-3-hydroxy-2,3-diphenylpropionitrile

Reaction of phenylacetonitrile and benzaldehyde on a 15 mmol scale according to the procedure in Example 1, and recrystallization from toluene/hexane gave 1.81 g of the desired anti-aldol product (53%). NMR ($^1$H, $^{13}$C), IR, and Mass spectra were consistent with the structure assigned previously by Wade et al. (J. Org. Chem. 52, 2973–2977 (1987)).

EXAMPLE 11

(2RS,3RS)-3-hydroxy-2,3-diphenylpropylammonium chloride

Following the procedure in Example 2, 2.60 mmol of (2RS, 3RS)-3-hydroxy-2,3-diphenylpropionitrile were reduced, affording 0.572 g (84%) of the desired primary amine hydrochloride, mp 236° C. (decomp.). NMR ($^1$H, $^{13}$C), IR, and Mass spectra were consistent with the assigned structure. Analysis: Calcd for $C_{15}H_{18}ClNO$: C, 68.30; H, 6.88; N, 5.31. Found: C, 68.30; H, 6.86; N, 5.21.

EXAMPLE 12

(2RS,3RS)-3-Hydroxy-2,3-diphenylpropyl-N, N-dimethyl-ammonium chloride

Following the procedure in Example 3, reductive methylation of 1.38 mmol of (2RS,3RS)-3-hydroxy-2,3-diphenylpropylammonium chloride afforded 0.385 g g (96%) of the desired tertiary amine hydrochloride, mp 59.3–63.8° C. NMR ($^1$H, $^{13}$C), IR, and Mass spectra were consistent with the assigned structure. HRMS (EI+): Calcd for $C_{17}H_{21}NO$ (M-HCl): 255.16231. Found: 255.16278.

EXAMPLE 13

(2RS,3RS)-3-hydroxy-2-phenyl-3-(2', 4', 6'-trimethylphenyl)propionitrile:

Reaction of phenylacetonitrile and mesitylaldehyde on a 8 mmol scale according to the procedure in Example 1, and recrystallization from toluene/hexane gave 1.32 g of the desired anti-aldol product (62%), mp 131.5–132.4° C. NMR ($^1$H, $^{13}$C), IR, and Mass spectra were consistent with the assigned structure. Analysis: Calcd for $C_{18}H_{19}NO$: C, 81.48; H, 7.21; N, 5.28. Found: C, 81.54; H, 7.23; N, 5.27.

EXAMPLE 14

(2RS,3RS)-3-hydroxy-3-(2',4',6'-trimethylphenyl)-2-phenyl propylammoniumchloride Following the procedure in Example 2, 1.5 mmol of (2RS, 3RS)-3-hydroxy-2-phenyl-3-(2',4', 6'-trimethyl-phenyl)-propionitrile were reduced, affording 0.376 g (82%) of the desired primary amine hydrochloride, mp 230° (decomp.). NMR ($^1$H, $^{13}$C), IR, and Mass spectra were consistent with the assigned structure. Analysis (as diacetate): Calcd for $C_{22}H_{27}NO_3$: C, 74.76; H, 7.70; N, 3.96. Found: C, 74.63; H, 7.78; N, 3.72.

EXAMPLE 15

(2RS,3RS)-3-Hydroxy-3-(2',4',6'-trimethylphenyl)-2-phenylpropyl-N,N-dimethylammonium chloride Following the procedure in Example 3, reductive methylation of 1.0 mmol of (2RS,3RS)-3-hydroxy-3-(2',4',6'-trimethylphenyl)-2-phenylpropylammonium chloride afforded 0.291 g (87%) of the desired tertiary amine hydrochloride, mp 84.2–86.9° C. NMR ($^1$H, $^{13}$C), IR, and Mass spectra were consistent with the assigned structure. HRMS (CI+) : Calcd for $C_{20}H_{28}NO$ (M-Cl) 298.21709. Found: 298.21777.

EXAMPLE 16

(2RS,3RS)-3-hydroxy-4,4-dimethyl-2-phenylpentanenitrile

Reaction of phenylacetonitrile and pivalaldehyde on a 30 mmol scale according to the procedure in Example 1, and recrystallization from toluene/hexane gave 5.34 g of the desired anti-aldol product (87%), m.p.: 70.7–71.2° C. NMR ($^1$H, $^{13}$C), IR, and Mass spectra were consistent with the assigned structure. Analysis: Calculated for $C_{13}H_{17}NO$: C, 76.81; H, 8.42; N, 6.89. Found: C, 76.80; H, 8.43; N, 6.83.

EXAMPLE 17

(2RS,3RS)-3-hydroxy-4,4-dimethyl-2-phenylpentylammonium chloride

Following the procedure in Example 2, 1.34 mmol of (2RS, 3RSI-3-hydroxy-4,4-dimethyl-2-phenylpentanenitrile were reduced, affording 0.252 g (77%) of the desired primary amine hydrochloride, mp 232.0–233.2° C. NMR ($^1$H, $^{13}$C), IR, and Mass spectra were consistent with the assigned structure. Analysis: Calcd for $C_{14}H_{22}ClNO$: C, 64.05; H, 9.10; N, 5.75. Found: C, 64.27; H, 9.17; N, 5.68.

EXAMPLE 18

(2R;, 3RS)-3-Hydroxy-4,4-dimethyl-2-phenylpentyl-N,N-dimethyl ammonium chloride

Following the procedure in Example 3, reductive methylation of 1.03 mmol of (2RS,3RS)-3-hydroxy-4, 4-dimethyl-2-phenylpentylammonium chloride afforded 0.242 g (87%) of the desired tertiary amine hydrochloride, mp 175.2–178.8° C. NMR ($^1$H, $^{13}$C), IR, and Mass spectra were consistent with the assigned structure. HRMS (CI+): Calcd for $C_{15}H_{26}NO$ (M-Cl): 236.20144. Found 236.20167.

What is claimed is:

1. The compound 3-hydroxy-4,4-dimethyl-2-(2'-naphthyl)pentyl-N,N-dimethylamine or a pharmaceutically acceptable salt thereof.

2. The compound of claim 1 which is the anti-diastereomer.

3. The compound 3-hydroxy-2-(2'-naphthyl)-phenylpropyl-N-N-dimethylamine or a pharmaceutically acceptable salt thereof.

4. The compound of claim 3 which is the anti-diastereomer.

5. The compound. 3-hydroxy-2-(2'-naphthyl)-3-phenylpropylamine or a pharmaceutically acceptable salt thereof.

6. The compound of claim 5 which is the anti-diastereomer.

7. A method for treating depression in a human, comprising administering to the human an effective antidepressant dose of the compound 3-hydroxy-4,4-dimethyl-2-(2'-naphthyl)pentyl-N,N-dimethylamine or a pharmaceutically acceptable salt thereof.

8. The method as claimed in claim 7, wherein said compound is the anti-diastereomer.

9. A method for treating depression in a human, comprising administering to the human an effective antidepressant dose of the compound 3-hydroxy-2-(2'-naphthyl)-3-phenylpropyl-N-N-dimethylamine or a pharmaceutically acceptable salt thereof.

10. The method as claimed in claim 9, wherein said compound is the anti-diastereomer.

11. A method for treating depression in a human, comprising administering to the human an effective antidepressant dose of the compound 3-hydroxy-2-(2'-naphthyl)-3-phenylpropylamine or a pharmaceutically acceptable salt thereof.

12. The method as claimed in claim 11, wherein said compound is the anti-diastereomer.

* * * * *